US012746027B2

(12) United States Patent
Hentrich et al.

(10) Patent No.: US 12,746,027 B2
(45) Date of Patent: Sep. 29, 2026

(54) WOUND CLEANSING DEVICE

(71) Applicant: Lohmann & Rauscher GmbH, Vienna (AT)

(72) Inventors: Axel Hentrich, Vienna (AT); Carina Tauscher, Markt Piesting (AT); Cornelia Häusler, Vienna (AT)

(73) Assignee: Lohmann & Rauscher GmbH, Vienna (AT)

( * ) Notice: Subject to any disclaimer, the term of this patent is extended or adjusted under 35 U.S.C. 154(b) by 962 days.

(21) Appl. No.: 17/271,542

(22) PCT Filed: Sep. 4, 2019

(86) PCT No.: PCT/EP2019/073568

§ 371 (c)(1),
(2) Date: Feb. 25, 2021

(87) PCT Pub. No.: WO2020/049038

PCT Pub. Date: Mar. 12, 2020

(65) Prior Publication Data

US 2021/0244431 A1 Aug. 12, 2021

(30) Foreign Application Priority Data

Sep. 4, 2018 (DE) ..................... 10 2018 121 501.0
Jan. 8, 2019 (DE) ..................... 20 2019 100 062.7

(51) Int. Cl.
*A61B 17/32* (2006.01)
*A46B 9/08* (2006.01)
(Continued)

(52) U.S. Cl.
CPC ............ *A61B 17/32* (2013.01); *A46D 1/0253* (2013.01); *A46D 1/0269* (2013.01);
(Continued)

(58) Field of Classification Search
CPC ...... A61F 13/00; A61F 13/02; A61F 13/0206; A61F 13/0209; A61F 13/0223;
(Continued)

(56) References Cited

U.S. PATENT DOCUMENTS 3,561,441 A * 2/1971 Lombardi ......... A61F 13/01021 602/44
9,713,553 B2 7/2017 Engl et al.
(Continued)

FOREIGN PATENT DOCUMENTS

DE 29924439 U1 4/2003
DE 102006049108 A1 4/2008
(Continued)

OTHER PUBLICATIONS

Schneider, Mechanical properties and cytotoxic evaluation of the Ti—3Nb—13Zr alloy, 2000.*
(Continued)

*Primary Examiner* — Alireza Nia
*Assistant Examiner* — Andrew Jun-Wai Mok
(74) *Attorney, Agent, or Firm* — Schwabe, Williamson & Wyatt, P.C.

(57) ABSTRACT

The invention relates to a wound cleansing device comprising a number of strand-shaped cleansing elements, characterized in that the cleansing quotient R=(E*F)/l of at least some cleansing elements is 0.05 N/mm or larger, particularly 0.1 N/mm or larger, preferably 1 N/mm or larger, particularly preferably 10 N/mm or larger and smaller than 1000 N/mm, preferably less than 500 N/mm, in particular 100 N/mm or smaller, wherein E denotes the modulus of elasticity of the material of which the cleansing elements are made, F denotes the average cross-sectional area of the
(Continued)

cleansing elements in a direction perpendicular to the strand axis, and l denotes the effective length of the cleansing elements.

16 Claims, 1 Drawing Sheet

(51) Int. Cl.

| | |
|---|---|
| ***A46D 1/00*** | (2006.01) |
| ***A61B 17/00*** | (2006.01) |
| ***A61F 13/00*** | (2024.01) |
| ***A61F 13/01*** | (2024.01) |
| ***A61F 13/05*** | (2024.01) |

(52) U.S. Cl.
CPC ......... *A46D 1/0284* (2013.01); *A46D 1/0292* (2013.01); *A46B 9/08* (2013.01); *A61B 2017/00747* (2013.01); *A61B 2017/320004* (2013.01)

(58) Field of Classification Search
CPC .............. A61F 13/0246; A61F 13/0253; A61F 2013/00089; A61F 2013/00255; A61L 31/00; A61L 31/14; A61L 31/146; A61L 15/44; A61L 26/0066; A61B 17/32; A61B 2017/00743; A61B 2017/00747; A61B 2017/320004–320012; A46B 9/00; A46B 9/08–12; A46D 1/00; A46D 1/02; A46D 1/0253–0292; A61K 9/70
See application file for complete search history.

(56) References Cited

U.S. PATENT DOCUMENTS

| | | | | | |
|---|---|---|---|---|---|
| 2003/0079324 | A1 | 5/2003 | Collins et al. | | |
| 2004/0265534 | A1* | 12/2004 | Curro | A61F 13/512 | 442/337 |
| 2010/0143431 | A1* | 6/2010 | Landau | A01N 59/16 | 204/192.15 |
| 2010/0163073 | A1* | 7/2010 | Lyngstadaas | A46B 3/18 | 134/8 |
| 2013/0101805 | A1* | 4/2013 | Altshuler | B32B 3/30 | 264/109 |
| 2015/0157508 | A1 | 6/2015 | Blott et al. | | |
| 2018/0000501 | A1* | 1/2018 | Baym | A61B 34/32 | |

FOREIGN PATENT DOCUMENTS

| | | | | |
|---|---|---|---|---|
| DE | 102012100842 A1 | 8/2013 | | |
| DE | 202019100062 U1 | 1/2019 | | |
| DE | 102018121501 A1 | 3/2020 | | |
| EP | 2077976 B1 | 7/2009 | | |
| EP | 2365794 B1 | 9/2011 | | |
| EP | 2777662 A1 * | 9/2014 | | A61F 13/00 |
| WO | 2010085831 A1 | 8/2010 | | |
| WO | 2014137824 A1 | 9/2014 | | |
| WO | WO-2016054854 A1 * | 4/2016 | | A46B 9/04 |

OTHER PUBLICATIONS

Lin C, Apr. 14, 2016, Multifilament-twisted toothbrush bristle.*
Contrado, Feb. 16, 2018, What is Velour and How Does it Differ From Velvet?*
Mass V, Sep. 17, 2014, Use Of A Velvet Fibrebonded Fabric Substance.*
Kramer Industries, Inc., Nov. 25, 2013, Mesh vs. Grit.*
Fibrous and Composite Materials for Civil Engineering Applications, 2011, Multifilament Yarn.*
International Search Report mailed Mar. 12, 2020, for International Application No. PCT/EP2019/073568, 6 pages.
International Preliminary Report on Patentability mailed Mar. 4, 2021, for International Application No. PCT/EP2019/073568, 6 pages.
CUTIMED DebriClean—All-Purpose Debridement Product Brochure, Apr. 2019, 4 pages with English translation.
Franck, Adolph, Kunststoff-Kompendium, 2000, pp. 80-81, 250-257, and 294-299, 15 pages with English abstract.
Rajendran, S., Advanced textiles for wound care, Woodhead Publishing in Textiles 2009, pp. 48-96.
Sachsisches Textilforschungsinstitut e.V. (STFI) Explanatory notes on the investigations carried out as part of order P2023 1082, May 31, 2023, 32 pages with English translation.
Thieme Rompp, Polyethylene terephthalates (PET) Article, Jun. 2002, 6 pages with English translation.
Wikipedia, Antimicrobial agents, last edited Jan. 6, 2019, 4 pages with English translation.
Wikipedia, Fineness (textiles), last edited Feb. 1, 2019, 20 pages with English translation.
Bunsell, A.R., Handbook of tensile properties of textile and technical fibers, Woodhead Publishing in Textiles, 2009, 684 pages.
Probst, Ines et al., Antimicrobial surface coating kills multidrug-resistant pathogens, Space Medicine Aviation and Travel Medicine 2016; 23 (5), pp. 217-220, 8 pages with English translation.
CUTIMED® DebriClean Product Description, Jun. 5, 2018, 4 pages.
CUTIMED® DebriClean Tips for Use, Mar. 2019, 5 pages with English translation.
CUTIMED® DebriClean the Innovative, Safe, and Effective Debridement Pad, Apr. 2019, 3 pages with English translation.
CUTIMED® DebriClean evaluation of debridement efficacy, EWMA 2019, Jun. 5-7, 2019, 1 page.
Essity, Center of Excellence Wound Care, Introduction of DebriClean (Debridement Pad), Presentation given Aug. 5, 2019, 60 pages with English translation.

* cited by examiner

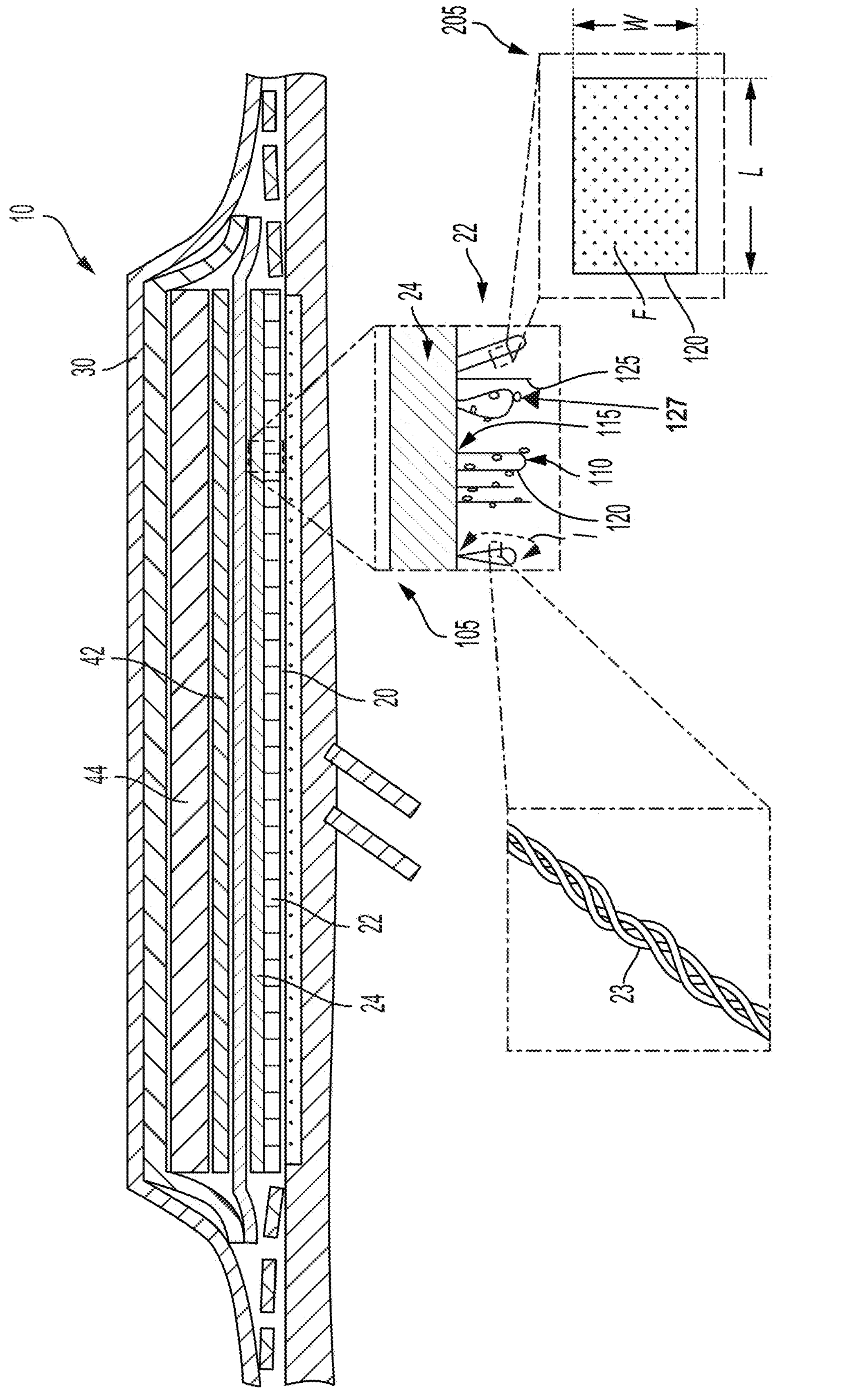
10
30
42
44
20
22
24
22
24
105
110
115
120
125
127
I
205
W
L
F
120
23

WOUND CLEANSING DEVICE

CROSS REFERENCE TO RELATED APPLICATION

The present application is a 35 U.S.C. § 371 national phase entry application of, and claims priority to, International Patent Application No. PCT/EP2019/073568, filed Sep. 4, 2019, which claims priority to German Patent Application No. DE 20 2019 100 062.7, filed Jan. 8, 2019, and DE 10 2018 121 501.0, filed Sep. 4, 2018, the disclosures of which are hereby incorporated by reference in their entirety for all purposes.

BACKGROUND

The invention relates to a wound cleansing device having a wound cleansing layer preferably comprising a number of strand-shaped cleansing elements. Such wound cleansing devices are for example indicated in EP 2 365 794. In the wound cleansing device described in this document, the strand-shaped cleansing elements are designed in the form of threads, wherein said threads can also be present in the form of monofilament fibers.

Prior art wound cleansing devices can be used to perform particularly gentle debridement. Debridement is a process of wound bed preparation in which substances formed by the body itself, that is, human material such as excessive fluids, fibrin coverings, dead epidermal tissue such as excessive keratinous material or dead corneocytes and/or plaques of dead tissue (necroses) are removed. The known wound cleansing device is designed as a wound cleansing cloth, wherein the cleansing elements configured as threads project from a carrier layer. They form a pile in which the effective length of the threads, also called the pile height, between the carrier layer and the ends of the threads facing away from the carrier layer is between 3 and 30 mm and the threads have between 0.5 and 20 dtex.

Although the known wound cleansing devices can be used with good results for treating many wounds, particularly severely exuding wounds, wound cleansing using the known wound cleansing devices proved to be problematic in other cases.

In view of these problems in prior art, it is the underlying problem of the invention to provide a wound cleansing device for extended applications.

According to the invention, this problem is solved by a further development of the known wound cleansing devices in which the cleansing quotient $R=(E*F)/l$ of at least some, preferably 5% or more, particularly 15% or more, of the cleansing elements is 0.05 N/mm or larger, particularly 0.1 N/mm or larger, preferably 1 N/mm or larger, particularly preferably 10 N/mm or larger and smaller than 1000 N/mm, preferably less than 500 N/mm, in particular 100 N/mm or smaller, wherein E denotes the modulus of elasticity of the material of which the cleansing elements are made, F denotes the average cross-sectional area of the cleansing elements in a direction perpendicular to the strand axis, and l denotes the effective length of the cleansing elements.

It was found that inadequate wound cleansing using the known wound cleansing devices is due to the use of particularly soft and long fibers which, while ensuring gentle wound bed preparation, are in many cases not suitable to detach from the wound and/or pick up persistently adhering substances, as are common in burn wounds, necroses, or some fibrin coverings.

It was found as part of the invention that, particularly when treating the burn wounds, necroses, and persistent fibrin coverings just mentioned, a balanced trade-off can be found between satisfactory cleansing on the one hand and still acceptable mechanical strain on the wound in the process of cleansing if the cleansing quotient is set in the range between 0.1 and 1000 N/mm, particularly between 1 and 500 N/mm, preferably between 10 and 100 N/mm.

The cleansing elements used as part of the invention may optionally comprise chemical fibers designed as staple fibers, particularly monofilaments, made of a synthetic material if it is ensured that the cleansing quotient is set between 1 and 1000 N/mm by enlarging the cross sectional area of the monofilaments and/or by shortening the effective length of the monofilaments. In addition, or alternatively, the wound cleansing device according to the invention may also comprise natural fibers, particularly in the form of staple fibers. Cellulose fibers are addressed as natural fibers within the context of this invention. If the cleansing elements form a pile as in the known wound cleansing devices, the effective fiber length denotes the length of the fibers between their anchoring in a carrier layer and the ends of the fibers facing away from the carrier layer.

If the cleansing elements configured as staple fibers, particularly monofilament fibers or multifilaments, for a cleansing fleece, the cohesion of the fleece results from the entanglement of individual fibers, merging of the fibers at contact points, needling of the fibers, or the like. An effective length of the staple fibers is available for cleansing between the entanglement areas, the contact points, and/or the needling areas, wherein a desired cleansing effect while maintaining a still acceptable mechanical strain on the wound can be achieved by respective adjustment of the effective length, the cross section of the fibers, and the modulus of elasticity.

Within the context of this invention, the effective length of the cleansing elements forming a cleansing fleece is defined as half the mean length of the staple fibers forming the fleece. If the fleece is made of staple fibers having a mean length (staple) of about 20 mm, the effective length, according to definition, is 10 mm.

According to the invention, at least some of the cleansing elements can be designed in the form of loops extending from the carrier layer. In this case, the effective length is defined as half the length of the loop, measured between two points at which the loop exits the carrier layer. The effective length of the loops can also be called the pile height of the pile formed by these loops.

It has proven expedient, particularly for loop-shaped cleansing elements, if at least some of these cleansing elements are optionally designed as twisted bundles of two, three, or more monofilaments. Monofilaments of these cleansing elements can have a cleansing quotient of less than 0.05 N/mm if the cleansing quotient of the bundles formed by the monofilaments is greater than 0.05 N/mm. As used herein, the term twisted denotes a structure in which the individual monofilaments circulate about a common helix axis. The loop-shaped cleansing elements can also be combined with other cleansing elements, such as cleansing elements designed to project freely on their ends facing away from the carrier layer.

Within the context of the invention, the use of cleansing elements in the form of wound cleansing devices containing continuous fibers is also considered. In this case, the effective length denotes the mean distance between contact points of the fibers or the mean distance between fiber intersections in a projection onto a plane running parallel to a main area of an optionally cloth-like wound cleansing device. The number of fiber layers approximately corresponds to the quotient of the thickness of the wound cleansing device in a direction perpendicular to the projection direction and the mean fiber diameter.

A flexibility of the cleansing elements just sufficient to prevent damage to the individual cleansing elements can be achieved if the fibers have a diameter of 500 μm or less, particularly 150 μm or less. On the other hand, detachment of individual fibers without excessive compression of the fleece can still be satisfactorily prevented if the diameter of the fibers is 10 μm or more, preferably more than 20 μm, particularly more than 30 μm, particularly preferably 45 μm or more. Excessive compression of the fleece is also considered problematic under the aspect that there must be sufficient space available in the cleansing device for the substances removed from the wound. Similar to the explanation given in EP 2 365 794, these substances can be held in the cleansing device by electrostatic attraction when using cleansing devices according to the invention as well.

If the cleansing elements are designed in the form of an optionally twisted bundle of two, three, or more monofilaments, each monofilament of the bundle may have a diameter of less than 10 μm. It has proven favorable in this case as well if the thickness of the monofilaments forming the bundle is 5 μm or more to counteract detachment of individual fibers from the bundle.

In order to provide sufficient holding capacity for contaminants removed from the wound, it has proven favorable within the context of the invention if the effective length of the fibers is 2 mm or more, preferably 3 mm or more, particularly 6 mm or more. Adhesion of the individual cleansing elements before utilizing the maximum holding capacity for removed contaminants can be prevented if the effective length of the staple fibers is 20 mm or less, particularly 15 mm or less, particularly preferably 13 mm or less, optionally 11 mm or less.

It has proven particularly advantageous if the modulus of elasticity of the material of the staple fibers and/or continuous fibers is 135,000 N/mm2, particularly 100,000 N/mm2 or less, preferably 50,000 N/mm2 or less, particularly preferably 5000 N/mm2 or less, and/or 100 N/mm2 or more, particularly 250 N/mm2 or more, optionally 500 N/mm2 or more. When setting a greater modulus of elasticity, the fiber length must also be increased accordingly and/or the cross sectional area must be reduced accordingly, which can result in the problems mentioned above. The lower limit for the modulus of elasticity can be derived accordingly.

The use of cleansing elements in the form of bristles and/or hooks and/or mushrooms projecting from a carrier sheet is also considered within the context of the invention. For the reasons described in EP 2 365 794, it has proven expedient within the context of this invention as well to use synthetic bristles and/or hooks and/or mushrooms as cleansing elements.

When using cleansing elements in the form of bristles and/or hooks and/or mushrooms, the effective length denotes the height of the bristles or hooks or mushrooms in a direction perpendicular to the carrier sheet, while the cross sectional area denotes the cross sectional area in a section plane extending parallel to the carrier sheet at half the height of the mushrooms, hooks, and/or bristles. In mushroom or hook-shaped cleansing elements, the effective height also denotes the distance between the carrier sheet and a tangential plane running parallel to the carrier sheet at the vertex of the hooks or mushrooms. This definition is based on the thought that the portion of the hooks or mushrooms bent backwards towards them barely influences the flexibility of the hooks or mushrooms as a whole.

In order to provide sufficient holding capacity for contaminants removed from the wound, it has proven expedient if the effective length of the bristles and/or hooks and/or mushrooms is 10 mm or less, preferably 5 mm or less, particularly 3 mm or less. Excessive stiffness of the bristles and/or hooks can be prevented if the effective length is 0.2 mm or more, particularly 0.5 mm or more, particularly preferably 1 mm or more.

As regards sufficient holding capacity and still sufficient flexibility of the bristles and/or hooks and/or mushrooms, it has proven expedient if the mean cross sectional area of the bristles and/or hooks and/or mushrooms is 10-8 m2 or more and/or 10-6 m2 or less, preferably between 3*10-8 and 3*10-7 m2.

The bristles, hooks, or mushrooms may have a branching or bifurcation on their side facing away from the carrier sheet, such that two or more ends are formed on the side facing away from the carrier sheet, which can optionally be bent backwards towards themselves.

Again for the purpose of providing sufficient holding capacity for contaminants on the one hand and ensuring an areal cleansing effect on the other hand, it has proven expedient if more than 10, particularly 20 or more particularly preferably 30 or more bristles and/or hooks and/or mushrooms are provided per cm2 of the carrier sheet and/or less than 100, preferably 50 or less bristles and/or hooks and/or mushrooms are provided per cm2 of the carrier sheet.

The material of the bristles and/or hooks and/or mushrooms can have a modulus of elasticity of 135,000 N/mm2 or less, particularly 50,000 N/mm2 or less, particularly preferably 5000 N/mm2 or less and 100 N/mm2 or more, particularly 250 N/mm2 or more, optionally 500 N/mm2 or more.

It has proven particularly expedient within the context of the invention if at least some cleansing elements are made at least partially, preferably completely, of polyester, vinyl, polyethylene, polypropylene, aramid, cellulose, and/or a polyamide. It is also considered within the context of the invention to apply at least one abrasive to the surface of at least one cleansing element to enhance the cleansing effect. An aramid which can be used for the invention has a modulus of elasticity of about 100,000 N/mm2. Polyethylene which can be used for the invention may have a modulus of elasticity between 95,000 and 135,000 N/mm2. Cellulose that can be used for producing wound cleansing devices according to the invention may have a modulus of elasticity between 3000 N/mm2 (viscose) and 100,000 N/mm2 (flax). Staple fibers made of polypropylene may have a modulus of elasticity of 5000 N/mm2. Polyamide fibers may have a modulus of elasticity between 250 N/mm2 and 3500 N/mm2.

The abrasive for the invention may comprise corundum, zirconium or aluminum oxide, silicon carbide, boron nitride, boron carbide, ceramic, chromium oxide, flint, quartz, emery, garnet, boron nitride, particularly cubic boron nitride, and/or diamond. The abrasive may in this context have a granulation in the range between 16 and 1200 mesh (according to DIN 69176), particularly between 150 and 800 mesh.

According to another aspect of the invention, the wound cleansing device according to the invention comprises at least one wound cleansing layer adapted for detaching substances from a wound and for holding the detached substances, preferably comprising a number of strand-shaped wound cleansing elements, wherein said wound cleansing layer may include two, three, or more wound cleansing regions having differing wound cleansing properties. The wound cleansing regions may for example be arranged in strips next to each other and/or on opposing sides of the wound cleansing device.

This aspect of the invention is based on the finding that wound cleansing problems observed in prior art are also due to the fact that geometrically separated regions can meet the requirements of wound cleansing particularly well if each region is optimized for a single process of wound cleansing. This is of particular significance when treating burns, necroses, and/or persistent fibrin coverings, wherein wound cleansing devices according to the invention may also have wound cleansing regions with conventional wound cleansing elements. These may promote pickup of fluids and plaques.

It was found that the geometrical separation of wound cleansing regions, each with optimized wound cleansing properties, all in all yields better wound cleansing results than optimization of the wound cleansing regions as a whole, as suggested in prior art, in that specific fiber structures are proposed which allow meeting different requirements by means of a single cleansing region.

It has proven particularly favorable in the context of the invention if one of the wound cleansing regions is an absorption region adapted to absorb wound fluid, particularly serous wound fluid. This absorption region can be designed in accordance with EP 2 365 794, that is, of chemical fibers and/or natural fibers, particularly monofilaments and/or multifilaments made of a synthetic material, having an effective fiber length of 2 mm or more, preferably 3 mm or more, particularly 6 mm or more. The effective fiber length, however, is preferably 15 mm or less, particularly 10 mm or less, because the use of longer fibers does no longer improve the absorption of serous substances with a low viscosity. The substances removed from the wound can be held between the individual fibers. This can prevent recontamination of the wound by substances previously removed. If the fibers of the absorption region according to EP 2 365 794 form a pile arranged on a carrier layer, the effective length of the fibers denotes the length of the fibers between the carrier layer and the end of the fibers facing away from the carrier layer.

If the fibers are designed as staple fibers and optionally form a cleansing fleece compressed by needling or water jets, the effective length for fibers having a (staple) length of 20 mm or less is defined as half the mean length of the staple fibers forming the fleece. For fibers having a (staple) length between 20 and 40 mm, the effective length is defined as a quarter of the mean length of the staple fibers forming the fleece. For fibers having a (staple) length of more than 40 mm, the effective length is defined as one eighth of the mean length of the staple fibers forming the fleece. If the fleece is made of staple fibers having a (staple) length of about 20 mm, the effective length, according to definition, is 10 mm. If the fleece is made of staple fibers having a mean length (staple) of about 30 mm, the effective length, according to definition, is 7.5 mm. If the fleece is made of staple fibers having a (staple) length of about 50 mm, the effective length, according to definition, is 6.25 mm.

Within the context of the invention, the use of wound cleansing layers formed by continuous fibers is also considered. In this case, the effective length of the fibers denotes the mean distance between contact points of the fibers or the mean distance between fiber intersections in a projection onto a plane running parallel to a main area of an optionally cloth-like wound cleansing device, multiplied by the number of fiber layers. The number of fiber layers approximately corresponds to the quotient of the thickness of the wound cleansing device in a direction perpendicular to the projection direction and the mean fiber diameter.

In a particularly preferred embodiment of the invention, one of the wound cleansing regions is an abrasion region adapted to remove fibrin coverings, dead tissue, keratinous material or the like. At least one abrasion region may be arranged between two absorption regions. The absorption region of wound cleansing devices according to the invention may comprise chemical fibers and/or natural fibers, particularly monofilaments and/or multifilaments, having an effective fiber length of 5 mm or less, preferably 3 mm or less, and/or the effective fiber length in an abrasion region arranged between two absorption regions may be 90% or less, particularly 50% or less, particularly preferably 30% or less of the effective fiber length of the absorption region. The effective length of the fibers in the abrasion region is preferably 0.5 mm or more, particularly 1.5 mm or more, and/or 5% or more, particularly 10% or more of the effective fiber length in adjacent absorption regions.

It was surprisingly found that the shorter fibers of the abrasion region, due to their greater stiffness, do not just benefit the removal of substances from the wound, but under specific conditions also improve the hooking of these substances. This surprising finding is due to the fact that adhesive bonds occur in the region of the fiber tips, particularly when removing exudates/fibrin coverings, which bonds render the utilization of the entire volume available between fibers of the absorption region impossible. If shorter fibers are used which benefit the removal of substances from the wound, a lesser degree of adhesive bonding is observed in the region of the fiber tips because the tips show a lesser tendency to adhere permanently due to their smaller deflection, such that, overall, more absorption capacity can be made available between the fibers, even if the available volume overall is smaller than the absorption volume available between longer fibers. Furthermore, the formation of cavities in the form of unused fiber regions under the adhesive bonds at the product surface can be reduced.

Furthermore, when arranging abrasion regions between absorption regions, substances removed with longer fiber lengths can also laterally penetrate into the absorption regions from the side in the area of transition between the abrasion region and the absorption region.

The known wound cleansing devices according to EP 2 365 794 can be used as a parent product for producing wound cleansing devices according to the invention, and abrasion regions can be produced using a laser cutter and/or heating roller and/or by shearing/trimming the fiber pile in desired patterns. The fiber ends are melted when using a laser cutter. The abrasion properties can be further optimized in this manner. When using a heat roller, the roller is rolled over the product. In this manner, the cleansing elements can be melted. It is also conceivable to cool the cleansing elements. The cleansing elements that are embrittled in this manner can then simply be broken for producing desired properties.

If a wound cleansing device according to EP 2 365 794 is used as the parent product for producing wound cleansing devices according to the invention, at least one abrasion region and at least one absorption region are arranged on a common carrier layer. In this case, the common carrier layer can substantially be flat, while the boundary surfaces of the absorption and abrasion regions facing away from the carrier layer form a profiled cleansing surface. Such wound cleansing devices are particularly useful for cleansing wounds that are greatly uneven, such as large ulcers, since the profiling on the boundary surface between absorption and abrasive regions facing away from the carrier layer makes it easy to reach different wound bed levels. This can cause effective wound cleansing.

Wound cleansing devices which consist exclusively of long fibers become heavy and unwieldy for wound cleansing when moistened by the fluids absorbed. The use according to the invention of absorption regions with long fibers and abrasion regions with short fibers reduces the weight and allows optimizing the dosing on the wound, since the wound bed can better be "palpated" and the wound bed levels can be evenly cleansed by adjusting the mechanical pressure to the respective region. As mentioned above, the capacity of the wound cleansing device can be utilized better because the longer fiber lengths can also be reached from the side (at the transition to the shorter fiber lengths) by exudate/fibrin. On the other hand, the longer fibers reduce the hardness or stiffness of the product, which again contributes to lesser mechanical strain on the wound and wound environment.

Furthermore, so-called mixed wounds (wounds typically have multiple viscosities) can be treated effectively because, as explained above, each fiber length of the cleansing layer has another optimum functional area with respect to effectiveness and mechanical capacity, the short fiber for harder/fibrinous plaques and/or fluids having a high viscosity or are very slow-moving, the long fiber for serous exudate (lower viscosity). Thus, multiple functional areas can be combined in one product. It can also be expected that hard debris can be held well in the alternating product fiber structure. Solid debris tends to "roll off" wound cleansing layers made of fibers of equal length.

In another embodiment of the invention, the carrier layer may be profiled and the boundary surfaces of the absorption and abrasion regions facing away from the carrier layer may be arranged in a common plane. In this embodiment of the invention, it is a particular advantage that the longer fibers of the absorption layer can hardly bend over the shorter fibers of the abrasion layer because they are held by the profiling of the carrier layer. Thus, abrasion and absorption properties can be maintained during the pressure applied to the wound cleansing device during wound cleansing. Such wound cleansing devices can be used particularly advantageously if harder substances or plaques, particularly fibrin coverings and/or necroses, must be removed from an otherwise serous exuding wound. In addition or alternatively, the carrier layer may comprise continuous section lines for profiling the carrier layer, such that the regions of the wound cleansing layer arranged to both sides of the section lines can be adjusted separately to the profile of the area to be cleansed, such as a wound area or an area around a wound. In this case, fibers of equal length can be used in the cleansing layer on both sides of the section line.

The wound cleansing devices according to the invention can not just be used to cleanse the wound itself, but also the skin surrounding the wound. It is not just human material that can be removed in this process. In addition or alternatively to removing human material, the wound cleansing devices according to the invention can be used to remove foreign material from the area of the wound and/or the skin surrounding the wound. Examples of foreign material include residues of ointments, such as zinc ointment, residues of adhesive patches or wound coverings, substances formed by adding water and/or aqueous or non-aqueous solutions of human material and the like.

In the embodiments explained above, the abrasion region is formed by fibers of a shorter length. In addition or alternatively, an abrasion region can also be formed by a seam running between two absorption regions. The seam optionally fastens the fibers of the absorption region to a carrier layer, resulting in a region of greater overall stiffness, which benefits the removal of substances from the wound. In addition or alternatively, an abrasion region can also be implemented by a sanding fleece of strand-shaped cleansing elements having a higher modulus of elasticity compared to the fibers of the absorption region and/or by an abrasive sheet with abrasive grains.

In wound cleansing devices according to the invention, abrasion regions can form a line, grid, or mesh structure separating the absorption regions from each other. The distance between two absorption regions separated from each other by an abrasion region is 10% or more, preferably 30% or more, particularly 50% or more, and/or 150% or less, particularly 100% or less, particularly preferably 90% or less of the effective fiber length of the fibers of the absorption region. The absorption regions may also be contiguous, like the abrasion regions. They may for example circulate helically. The distance between two absorption regions separated by an abrasion region may be 30 mm or less, particularly 10 mm or less, optionally 5 mm or less, and/or 0.1 mm or more, preferably 1 mm or more, particularly 3 mm or more.

As explained above, wound cleansing devices with wound cleansing layers of fibers having a short fiber length are particularly well suited for removing viscous fluids from wounds.

According to another aspect of the invention, which is assigned independent eligibility for protection within the scope of the invention, a wound cleansing device is provided having a wound cleansing layer adapted for removing substances from a wound and for hooking the substances, which device is substantially characterized in that the wound cleansing layer comprises chemical fibers and/or natural fibers, particularly monofilaments or multifilaments of a synthetic material having an effective fiber length of 5 mm or less, particularly 4 mm or less, particularly preferably 3 mm or less, and 0.5 mm or more, particularly 1.5 mm or more, particularly preferably 2.5 mm or more.

Within the context of the invention, providing a wound cleansing kit with a wound cleansing device according to the invention in sterile packaging is considered as well. An instruction for use of the wound cleansing device for treating burn wounds and/or necroses and/or persistent fibrin coverings and/or exuding wounds and/or fibrinous coverings may be provided in and/or on the pack.

As can be derived from the above explanation of wound cleansing devices and wound cleansing kits, a wound cleansing device according to the invention is particularly advantageously used for producing a therapy device for treating burn wounds, necroses, and/or fibrin coverings. The wound cleansing device according to the invention is suitable for use in the treatment of burn wounds, necroses, and/or fibrin coverings, and/or exuding wounds.

As regards the properties of natural fibers and/or chemical fibers suitable for producing wound cleansing devices according to the invention, we refer to EP 2 365 794, which in this respect is incorporated herein by express reference. According to this document, fibers used for producing wound cleansing devices according to the invention, that is, both for producing abrasion regions and for producing absorption regions, may have an effective length between 3 and 30 mm. The fibers may have a density between 0.5 and 30 dtex.

The abrasion regions of wound cleansing devices according to the invention may form a square pattern. The distance between adjacent absorption regions is defined as the edge length of these squares. They may also circulate helically. They may form wave-like lines. Abrasion regions extending radially from a joint center are considered as well. It is also possible to design the abrasion regions in the form of jagged lines between individual absorption regions. If the abrasion regions are formed by seam lines, the distance between individual seam lines can be between 20 and 90% of the effective fiber length in the absorption regions. In a preferred embodiment, the distance between the seam lines may be 0.5 to 3 cm, particularly about 0.7 cm. In another embodiment of the invention, the distance between the individual seam lines may be about 1 cm. When treating large-area wounds with accordingly dimensioned wound cleansing layers, the distance between seam lines may be 2 to 3 cm.

The width of abrasion regions arranged in strips between absorption regions, which abrasion regions may for example be obtained by machining a parent product according to EP 2 365 794 using a laser cutter and/or a heat roller, preferably is between 0.2 and 0.9 cm, particularly about 0.5 cm. In a respective parent product, continuous dividing lines can be applied at a spacing of 0.2 to about 1 cm using a laser cutter. If an abrasive fleece or an abrasive sheet is used, respective abrasion regions may also be arranged as longitudinal strips between individual absorption regions, wherein the width of the individual abrasion regions may be about 0.5 to 1.5 cm, preferably about 1 cm. In wound cleansing devices with a larger cleansing area, abrasion regions having a greater width of up to 5 cm may be used. In all embodiments of the invention, the abrasion regions can also be produced by cooling or "freezing" and subsequent breaking of the respective cleansing elements.

In other embodiments of the invention, it has been considered to arrange absorption and abrasion regions on opposing boundary surfaces of a joint carrier layer. In this embodiment of the invention, the wound cleansing layer arranged on one side of the carrier layer may have particularly good absorption properties, while the wound cleansing layer arranged on the opposite side of the carrier layer may have particularly good abrasive properties.

If the wound cleansing device according to the invention has only one cleansing layer with one cleansing region of fibers having a fiber length of 5 mm or less and 1.5 mm or more, viscous fluids can be removed from the wound and held with this layer particularly well. If both fibers having a short effective length and fibers having a comparatively long effective length are used, it has proven favorable if the proportion of the fibers having a short length is between 10 and 90%, preferably between 30 and 70%, particularly preferably about 50% of the total number of fibers. If the fibers have freely projecting fiber ends, the number of freely projecting fiber ends per cm2 of the wound cleansing layer is preferably about 102 to 108, preferably about 103 to 107, particularly preferably 104 to 106. The fibers forming the cleansing layer of wound cleansing devices according to the invention may at least partially, preferably completely, be made of polyester, nylon, vinyl, polyethylene, polypropylene, aramid, cellulose, and/or polyamide. Abrasives may be applied as an additional cleaning agent to the surfaces of the individual fibers.

According to another aspect of the invention, at least some cleansing elements or wound cleansing elements may at least be partially provided with an antimicrobial coating.

Such wound cleansing devices are for example described in WO 2010/085831 A1. In these known wound cleansing devices, the wound cleansing elements are configured in the form of individual synthetic fibers or monofilaments made of polyester which project from a carrier layer and have freely projecting ends on their side facing away from the carrier layer. The freely projecting ends produce a razor blade effect which benefits wound cleansing without impairing the wound healing process.

When using the known wound cleansing devices, it has also been considered to remove bacterial colonizations of the wound with a biofilm which results in systematic infection of the patient. To this end, the wound cleansing elements made of synthetic fibers can also be coated with an antimicrobially effective coating in known wound cleansing devices.

When using the known wound cleansing devices, it was found that infections of the wound will still occur in many cases, despite careful wound cleansing and the use of an antimicrobially effective coating.

Within the scope of this invention, these problems are solved by a further development of the known wound cleansing devices, which is substantially characterized in that the antimicrobial coating comprises two metals which differ from one another, preferably as bimetal particles.

The invention is based on the finding that conventional coatings hardly bring about their antimicrobial effect during wound cleansing. When cleansing wounds using wound cleansing devices according to the invention, the wound is wiped out using the wound cleansing elements. The contact time between wound cleansing elements and the wound bed or bacterial colonization of the wound, or the period of efficacy, is a few seconds at best. On the other hand, the mechanism of action of conventional antimicrobial coatings, for example based on silver, is that metal or silver ions are released and have their oligodynamic effect. The metal or silver ions, however, are released with a great delay, such that their antimicrobial action is not or barely started if the contact time is just a few seconds.

On the other hand, coatings with antimicrobially active substances in the form of large molecules, such as PHMB, only have a reduced penetration depth into the wound bed, which is also not sufficient to take the desired antimicrobial effect.

This aspect of the invention is based on the surprising finding that, unlike the assumption of EP 2 077 976 B1, the microbial effect when using coatings of two metals which differ from one another and are preferably present as bimetal particles is not due to the release of metal ions but to a catalytic effect with the help of which antimicrobial substances are generated on contact with aqueous media, particularly reactive oxygen species (ROS) such as hydrogen peroxide. Catalytic generation of the antimicrobially active substances using a coating containing two metal species takes place in contact with aqueous media on a time scale of clearly less than one second. Therefore, sufficient catalytic reaction to antimicrobially active products occurs at respective contact times between wound cleansing elements and the wound bed when wiping out a wound using wound cleansing devices designed according to this aspect. Furthermore, the antimicrobially active products in the form of ROS generated in this manner represent comparatively small molecules which exhibit sufficient penetration depth into the wound bed. Overall, bacterial colonization of the wound bed can be satisfactorily addressed using wound cleansing devices according to the invention.

If the metal species are present as bimetal particles, a contact potential is formed which further enhances the catalytic effect of the metal species. Another advantage of the antimicrobial coating used according to the invention is that the coating is not depleted, since the antimicrobial action is not due to the release of metal ions but to a catalytic effect. Therefore, continuous generation of new short-lived reactive substances, particularly ROS, may occur. The antimicrobial effect is therefore preserved during repeated use, such as wiping out the same wound multiple times using one and the same wound cleansing element.

It has been found particularly favorable within the context of the invention if the antimicrobial coating contains silver and/or ruthenium. The antimicrobial action of silver-ruthenium coatings has been described, for example, in EP 2 077 976 B1. The mechanism of action (release of silver ions) assumed there does not come into play when using respective coatings in conjunction with wound cleansing devices. It was surprisingly found that silver-ruthenium coatings promote the catalytic reaction of aqueous media to reactive oxygen species which can have an antimicrobial effect. Only this made the use of this coating useful in the context of wound cleansing by wiping out wounds.

Remarkably, the catalytic effect is enhanced if the antimicrobial coating comprises a vitamin and/or a vitamin derivative, wherein the vitamin preferably is ascorbic acid.

The thickness of the antimicrobially active coating on the cleansing elements preferably is less than 1 μm, particularly 800 nm or less. This ensures that the coating will not significantly change the mechanical fiber properties, even if fine fibers are used. To ensure the efficacy of the coating, it has proven expedient if the thickness of the coating is 100 nm or more, particularly 200 nm or more. The coating is expediently applied to the wound cleansing elements by physical vapor deposition (PVD) technologies.

In addition or alternatively, the antimicrobial coating may also comprise a surfactant. Like the wound cleansing devices described in WO 2010/085831 A1, the wound cleansing elements of a wound cleansing device according to the invention may project from a carrier layer, wherein at least some of the wound cleansing elements preferably comprise freely projecting ends on their side facing away from the carrier layer. In addition or alternatively, at least some of the wound cleansing elements may form loops which project from, and/or rest against, the carrier layer.

As can be derived from the above explanation of wound cleansing devices according to the invention, these are used particularly advantageously for debridement. The term debridement means wound bed preparation in which substances formed by the body itself or respective human material such as excessive fluids, fibrin coverings, dead epidermal tissue such as excessive keratinous material or dead corneocytes and/or plaques of dead tissue (necroses) are removed.

The invention is not limited to the use of silver-ruthenium-containing coatings. Instead, the use of coating with platinum-ruthenium, ruthenium-copper, and/or ruthenium-gold nanoparticles is considered as well.

Within the scope of the invention, the wound cleansing device can be provided in the form of a kit in which the wound cleansing device is contained in a sterile pack. An instruction for use of the wound cleansing device for treating burn wounds, necroses, and/or persistent fibrin coverings and/or biofilms and/or a bacterial load may be provided in and/or on the pack.

As can be derived from the above explanation of wound cleansing devices and kits, the invention also relates to a use of the wound cleansing device according to the invention for producing a therapy device for treating burn wounds, necroses, and/or fibrin coverings. To this end, the wound cleansing device according to the invention can be attached to a preferably flexible application rod. The application rod can optionally be equipped with a wound cleansing device according to the invention on both sides. In other embodiments of the invention, the wound cleansing device can also be designed as a modular system having a cleansing head which may optionally be detachably attached to an application rod, wherein said cleansing head comprises a wound cleansing device according to the invention. Furthermore, a wound cleansing device according to the invention may also be designed in the form of a glove.

Also considered within the scope of the invention is the use of wound cleansing devices having two, three, or more cleansing regions, wherein one of the cleansing regions may comprise cleansing elements in the form of hooks, bristles, and/or mushrooms and another cleansing region may be equipped with fiber or filament-shaped cleansing elements. The cleansing quotient of the filaments and/or fibers may be less than 0.05 N/mm.

It was surprisingly found in the context of the invention that wound cleansing devices according to the invention can not just be used for wound cleansing itself, but also for follow-up wound treatment using a suitable wound dressing, particularly as part of the so-called negative pressure or vacuum therapy.

During negative pressure therapy, a negative pressure is generated in the wound space. The wound space is to this end typically clad with an optionally absorbent filler material which is not only used to absorb the exudate but also to evenly distribute the negative pressure across the entire wound surface. The wound or the filler material is covered with a suitable cover means, such as a film. An airtight cover means can often be used, which however is permeable to water vapor to prevent excessive drying out of the wound and maceration in the area of the wound edges.

The wound space closed off using of the cover means and containing wound filler material is typically connected to a negative pressure source, such as a pump, using a drainage tube. The negative pressure or suction applied via the pump and the tube promotes active wound cleansing by removing excessive wound exudate, cell debris, and bacteria from the wound. This also reduces wound edemas and thus improves blood circulation in the wound area. The formation of granulation tissue is accelerated as well. It is assumed that acceleration of granulation tissue formation is due to the fact that the negative pressure and the associated stretching of the cells stimulate the tissue to increased cell proliferation, angiogenesis, and formation of tissue matrix.

The cover means and the filler material are removed from the wound in the course of the negative pressure therapy. It was found that wound healing with conventional negative pressure therapy arrangements is often unsatisfactory.

The problems of wound healing in conjunction with negative pressure therapy are solved within the scope of the invention by providing a wound dressing having a wound contact layer with a number of strand-shaped wound contact elements and a preferably airtight but water vapor permeable cover means which can be fastened by adhesion to the skin surrounding the wound. This aspect of the invention is based on the finding that the problems observed in conventional negative pressure therapy are due to the use of a conventional wound sponge as filler material, which causes the tissue to grow around and into the three-dimensional sponge structure. When the wound dressing is changed, connecting webs into the sponge structure yield to a limited extent only, and the tissue can be injured again when pulling off the wound dressing.

This deficiency is remedied by using a wound contact layer having a number of strand-shaped wound contact elements, which may for example be formed by a wound cleansing device according to the invention. The healing tissue can grow in between the individual wound contact elements, is not injured when the dressing is changed because the many wound contact elements are pulled from the healing wound surface individually and without being obstructed by other wound contact elements. Not only wound cleansing devices according to the invention but also wound cleansing devices known from EP 2365794 can be used for producing a wound dressing according to the invention, for example. It is essential that the wound contact layer is formed by a plurality of wound contact elements between which there is sufficient space to allow ingrowth of the healing tissue, wherein the individual volume segments of this space are open on their side facing the wound and allow removal of the wound contact elements from the tissue that may have grown in.

Furthermore, the use of wound contact layers having a number of strand-shaped wound contact elements also helps form a granulation layer which promotes wound healing. In addition, the individual wound contact elements can also promote accelerated wound healing by mechanically stimulating the wound tissue. This is achieved by a proliferation-increasing stimulation of the tissue through so-called “micro needling.” The movement of the individual wound contact elements can mechanically stimulate the tissue and thus cause increased cell proliferation. The mechanical movement can for example be generated by an external input of mechanical energy, the patient’s own movement, an excited piezo crystal, ultrasound, and/or intermittent negative pressure.

The wound-healing effect of wound dressings according to the invention having a number of strand-shaped wound contact elements can also be explained in that deep wound cleansing is promoted by the wound contact elements during use and optionally be enhanced by relative movement between wound contact elements and the wound surface in a mobile patient. Furthermore, increased pickup and improved removal of exudate are observed as well if the dressing according to the invention comprises hydrophilic fibers.

A dressing according to the invention can be implemented as a prefabricated dressing with integrated wound contact elements, which are optionally provided by a wound cleansing device according to the invention. It is also envisaged to combine the wound cleansing device according to the invention and a conventional wound dressing into a kit, wherein the wound cleansing device is added to the conventional wound dressing for optional wound filling.

The wound dressing according to the invention may comprise an absorption and/or distributing layer arranged between the wound contact layer and the cover means. The cover means of a dressing according to the invention can be provided in the form of a film, such as a polyurethane film.

As can be derived from the above explanation of negative pressure therapy arrangements, it has proven expedient within the context of the invention if the cover means is associated with a connecting means adapted to connect a fluid line which connects the wound space to a negative pressure source.

The use of a wound cleansing device for producing a dressing which can be used for negative pressure therapy is also claimed within the scope of the invention. This aspect of the invention also relates to a wound cleansing device according to the invention for use in negative pressure therapy.

BRIEF DESCRIPTION OF THE DRAWINGS

FIG. 1 of the drawing shows a wound dressing, in accordance with various embodiments.

DETAILED DESCRIPTION

FIG. 1 shows a wound dressing 10 according to the invention. This wound dressing comprises a wound cleansing device 20 according to the invention and a cover means 30 in the form of a water vapor permeable backing film, which may be designed as a polyurethane film. The wound cleansing device 20 comprises a carrier layer 24 and a plurality of wound cleansing elements 22 on its side facing the wound, which elements can be used as wound contact elements of a wound dressing according to the invention. The wound cleansing elements 22 are only schematically represented in the drawing. They can be implemented in the form of a fiber fleece or the like. The wound cleansing elements 22 may also be implemented in the form of individual loops, hooks, bristles, and/or mushrooms. In addition, mixtures of fibers, loops, bristles, hooks, and/or mushrooms may be used. At least some of the cleansing elements 22 are optionally designed as twisted bundles of two, three, or more monofilaments 23.

Specifically, portion 105 depicts a “blown-up” view of a portion of the wound dressing 10 showing a more detailed view of a portion of the carrier layer 24 and the wound cleansing elements 22. As shown, the wound cleansing elements 22 may be implemented as loops 120 and/or bristles 125 (amongst other shapes as previously described), and may include abrasive 127 on a surface of the wound cleansing elements 22, to form an abrasion region. If implemented as loops 120, the loops 120 may have points 115 at which they exit/enter/attach to the carrier layer 24. As such, the effective length l of a loop may be the half distance between points 115 of the loop. To put it another way, the effective length l of a loop may be the distance between a point 115 of the loop and a midpoint 110 of the loop as shown in FIG. 1.

FIG. 1 also shows portion 205 which depicts a cross-sectional area F of an element 120. For example, element 120 is depicted in portion 205 as rectangular with a length L and a width W and so, in this depiction, the cross-sectional area F would be equal to the value L×W. In other embodiments if the element 120 had a different cross-sectional shape (e.g., circular, oval, square, etc.), then the equation to assess the value of F may be different.

A distributing layer 42 and an absorption layer 44 which may optionally be designed as airlaid nonwoven are provided between the wound cleansing device 20 and the cover means 30. The distributing layer 42 is arranged on the side of the absorption layer 44 that faces the wound cleansing device 20.

The invention claimed is:

1. A wound cleansing device for the debridement of a wound, the wound cleansing device comprising: a carrier layer; and a wound cleansing layer comprising a plurality of strand-shaped cleansing elements; wherein: a cleansing quotient $R=(E*F)/l$ of at least some cleansing elements of the plurality of strand-shaped cleansing elements is between 0.05 Newtons per millimeter (N/mm) and 1000 N/mm, E denotes a modulus of elasticity of a material of which at least some cleansing elements of the plurality of strand-shaped cleansing elements are made, F denotes an average cross-sectional area of at least some cleansing elements of the plurality of strand-shaped cleansing elements in a direction perpendicular to a strand axis, and l denotes an effective length of at least some cleansing elements of the plurality of strand-shaped cleansing elements; at least some cleansing elements of the plurality of strand-shaped cleansing elements form loops that extend from the carrier layer, and wherein each loop of a plurality of loops has a length as measured from a first point at which each loop protrudes from the carrier layer to a second point at which each loop protrudes from the carrier layer, and wherein the length is twice the effective length, wherein at least some of the cleansing elements forming loops of the plurality of strand-shaped cleansing elements are twisted bundles of a plurality of monofilaments, wherein at least some cleansing elements of the plurality of strand-shaped cleansing elements project freely on their ends facing away from the carrier layer, and the wound cleansing layer is configured to debride the wound, wherein debridement of the wound includes detaching substances from the wound and holding the detached substances.

2. The wound cleansing device of claim 1, further comprising an abrasive on a surface of a cleansing element of the plurality of strand-shaped cleansing elements.

3. The wound cleansing device of claim 2, wherein the abrasive includes corundum, zirconium, silicon carbide, boron nitride, chromium oxide, flint, emery, garnet, boron nitride, cubic boron nitride, or diamond.

4. The wound cleansing device of claim 3, wherein the abrasive has a granulation between 50 and 1000 mesh.

5. The wound cleansing device of claim 1, wherein at least some cleansing elements of the plurality of strand-shaped cleansing elements comprise chemical fibers that include monofilaments or multifilaments of a synthetic material.

6. The wound cleansing device of claim 2, wherein the chemical fibers have a diameter of less than or equal to 500 micrometers (μm).

7. The wound cleansing device of claim 2, wherein the chemical fibers have a diameter of greater than or equal to 5 micrometers (μm).

8. The wound cleansing device of claim 1, wherein a cleansing element of the plurality of strand-shaped cleansing elements includes an antimicrobial coating, and the antimicrobial coating includes two metals that differ from one another and are present as bimetal particles.

9. The wound cleansing device of claim 8, wherein the antimicrobial coating includes silver or ruthenium.

10. The wound cleansing device of claim 8, wherein the antimicrobial coating includes a vitamin or a vitamin derivative, and wherein the vitamin is ascorbic acid.

11. The wound cleansing device of claim 8, wherein the antimicrobial coating includes a surfactant.

12. The wound cleansing device of claim 1, wherein the effective length is greater than or equal to 3 mm.

13. The wound cleansing device of claim 1, wherein the effective length is less than or equal to 11 mm.

14. The wound cleansing device of claim 1, wherein the modulus of elasticity is between 500 $N/mm^2$ and 50,000 $N/mm^2$.

15. The wound cleansing device of claim 1, wherein at least some cleansing elements of the plurality of strand-shaped cleansing elements includes polyester.

16. The wound cleansing device of claim 1, wherein the cleansing quotient R is less than or equal to 100 N/mm.

* * * * *